(12) United States Patent
Reiner (10) Patent No.: US 6,196,686 B1
(45) Date of Patent: Mar. 6, 2001

(54) OPTIC SYSTEM FOR VIEWING AND FOR PHOTOGRAPHING THE INSIDE OF AN EYE

(75) Inventor: Josef Reiner, Köln (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 0 days.

(21) Appl. No.: 09/421,048

(22) Filed: Oct. 19, 1999

(30) Foreign Application Priority Data

Oct. 29, 1998 (DE) .......................................... 298 19 341 U (51) Int. Cl.$^7$ ....................................................... A61B 3/10
(52) U.S. Cl. ............................................ 351/221; 351/219
(58) Field of Search ..................................... 351/205, 206, 351/212, 219, 221, 247, 160 R (56) References Cited

U.S. PATENT DOCUMENTS 3,589,800 * 6/1971 Cardona ................................ 351/221
5,822,036 * 10/1998 Massie et al. ......................... 351/219

* cited by examiner

Primary Examiner—George Manuel
(74) Attorney, Agent, or Firm—Flynn, Thiel, Boutell & Tanis, P.C.

(57) ABSTRACT

An optic system for viewing the inside of the eye with a lens system. The lens system has a concave lens surface configured to be placed onto the cornea of an eye. The lens system has furthermore at least one further lens arranged in viewing direction in front of the first lens. The area to be viewed is also illuminated, whereby this illumination will not result in reflexes on optical surfaces. Furthermore, such an optic system is small, lightweight and compact that it neither interferes during a pre-surgical or post-surgical diagnosis nor during surgery. The optic system has for this purpose an illuminating device, the light-exiting surface of which lies within the first lens, or terminates flush with a lens surface of the first lens.

24 Claims, 7 Drawing Sheets

OPTIC SYSTEM FOR VIEWING AND FOR PHOTOGRAPHING THE INSIDE OF AN EYE

FIELD OF THE INVENTION

The invention relates to an optic system for viewing the inside of an eye with a lens system having a first lens with a concave lens surface which can be placed onto the cornea of an eye, and at least one further lens which is arranged in viewing direction in front of the first lens.

BACKGROUND OF THE INVENTION

Optic viewing systems are of great importance for diagnosing eye diseases and also for surgeries inside of the eye. Two methods have here proven to be particularly advantageous. It is the ophthalmoscopy in the upright image, during which the viewer uses the optic eye system of the eye of the patient as a magnifying lens, and the ophthalmoscopy in the reversed image, during which an additional ophthalmoscopy lens must be used. Mirror images result with these two methods, which are created when light is introduced from outside into the inside of the eye, in the cornea front surface, and in the case of the method with the reversed image in addition on the surfaces of the ophthalmoscopy lens.

Known are a number of ophthalmoscopes and retina cameras, which have been designed in accordance with the reflex-free viewing principle. With these it is possible to reflex-free view the inside of the eye. They are also suitable for the diagnosis of eye diseases, which cause visible changes inside of the eye. Because of their complex design and their dimensions, such devices, however, cannot be utilized during eye surgeries. Surgery microscopes have been used in eye surgeries for several decades. These are stereomicroscopes of a weak enlargement, which enable an excellent viewing of the eye, however, only in the front eye section.

However, surgeons need surgery microscopes, with which they can view actions also inside of the eye. This is possible when a lens with a strong negative action is placed onto the cornea of the patient. An immersion fluid must exist between the eye and the lens. The action of the dispersing lens creates an image of the retina or of the inside of the eye at a distance, to which the microscope can be adjusted.

The endoillumination can be used to illuminate the inside of the eye, during which endoillumination a fiber-optic light conductor is guided through the sclera of the eye of the patient into the inside of the eye. The introduction of bodies of any type into the inside of the eye is always associated with great risk. An illumination from outside is therefore desired.

The purpose of the invention is to enable the viewing of an area of the inside of the eye, which area is as large as possible, whereby the viewed area is illuminated and no reflexes on optical surfaces result due to the illumination, no surgical procedure is needed for the illumination of the background of the eye, and the optic system is so small, lightweight and compact that it interferes neither during a presurgical or postsurgical diagnosis nor during a surgical procedure.

SUMMARY OF THE INVENTION

The purpose is attained in such a manner that the optic system has an illuminating device, the light-exiting surface of which lies within the first lens or ends flush with a lens surface of the first lens.

The optic system is placed onto the cornea of the eye in order to examine the eye, whereby an immersion fluid is fed by a hose between the cornea and the lens surface. The first lens is connected to a light-exiting surface such that light is guided for viewing into the inside of the eye. The light-exiting surface can thereby be provided in the lens or, however, can terminate flush with one of the two lens surfaces (convex and concave lens surface).

When the light-exiting surface is connected optically conductingly to the convex lens surface of the first lens, the light beams, which exit from the light-exiting surface, are guided directly into the first lens.

Whereas when the light-exiting surface terminates flush with the concave lens surface of the first lens, then the light from the light-exiting surface is guided into the immersion fluid and moves from there into the inside of the eye.

The light-exiting surface is arched advantageously concavely when it terminates with the concave surface of the first lens.

The light-exiting surface of the illuminating device can also be part of a prism, which is connected optically conductingly to one or several fiber-optic light conductors, or, however, the light-exiting surface is part of one or several fiber-optic light conductors themselves.

In order for light to exit from the fiber-optic light conductor, same must be optically connected to a light source.

The light-exiting surface can, however, also be part of a light source, preferably a light diode. The fiber-optic light conductor can be introduced in various ways into the optic system. According to the invention, the optic system can be designed such that the fiber-optic light conductor is introduced between the first lens and each further lens into the optic system. However, it is also possible according to the invention that the fiber-optic light conductor is introduced through the further lenses into the optic system. A hose for the immersion fluid is advantageously guided parallel with the fiber-optic light conductor, which hose terminates on the concave side of the first lens.

However, the purpose can also be attained in such a manner that a semitransparent reflection surface is inserted between the first and the second lens, the main plane of which reflection surface is inclined approximately 45° with respect to the optic axis of the optic system, that a lateral light inlet into the optic system is provided in the area of the reflection surface, whereby the semitransparent reflection surface can be deflected into the viewing direction.

The semitransparent reflection surface can be formed either by a mirror or by at least one prism. The semitransparent reflection surface can according to the invention be arched.

At least one lens can be inserted according to the invention between the reflection surface and the light inlet, whereby we are preferably dealing with a collective lens.

It is advantageous for both solutions of the purposes that the lenses and the further details of the optic system are assembled releasably in one housing, and that also the housing is sealed off and is protected against stray-light entry. It is particularly advantageous when the first lens is a concave-convex lens and one single further lens is a biconvex lens.

In order to be able to guarantee the reuse during surgeries, it is particularly advantageous when the optic system can be sterilized and/or autoclaved. The optic system can according to the invention be enlarged by means of a mounted holder for additional lenses. Furthermore, the optic system can be provided with an image-viewing and/or image-receiving device.

BRIEF DESCRIPTION OF THE DRAWINGS

Various exemplary embodiments will be described in connection with the drawings. FIGS. 1–6 of the drawings each have a part A and a part B. Parts B each show a plan view of the optic system and in parts A a cross section of the optic system along the section line indicated in each part B.

The drawings show in detail:

DETAILED DISCUSSION

The exemplary embodiments illustrated in FIGS. 1–6 take care of the first attainment of the purpose of the invention. The optic system is placed with the concave lens surface 1a of the concave-convex lens onto an eye of the patient. Immersion fluid is introduced by a hose 15 (schematically illustrated) to the region between the concave lens surface 1a and the cornea. The beams of light viewed inside of the eye travels through the immersion fluid into the concave-convex lens 1, which is followed by the biconcave lens 2. Both lenses are mounted in the housing 3. A fiber-optic light conductor 4 is guided through the biconcave lens 2 onto the concave lens surface 1a of the concave-convex lens 1 in order to illuminate the eye. The light-exiting surface 8 terminates flush with the concave lens surface 1a of the concave-convex lens 1.

Figure 1A:
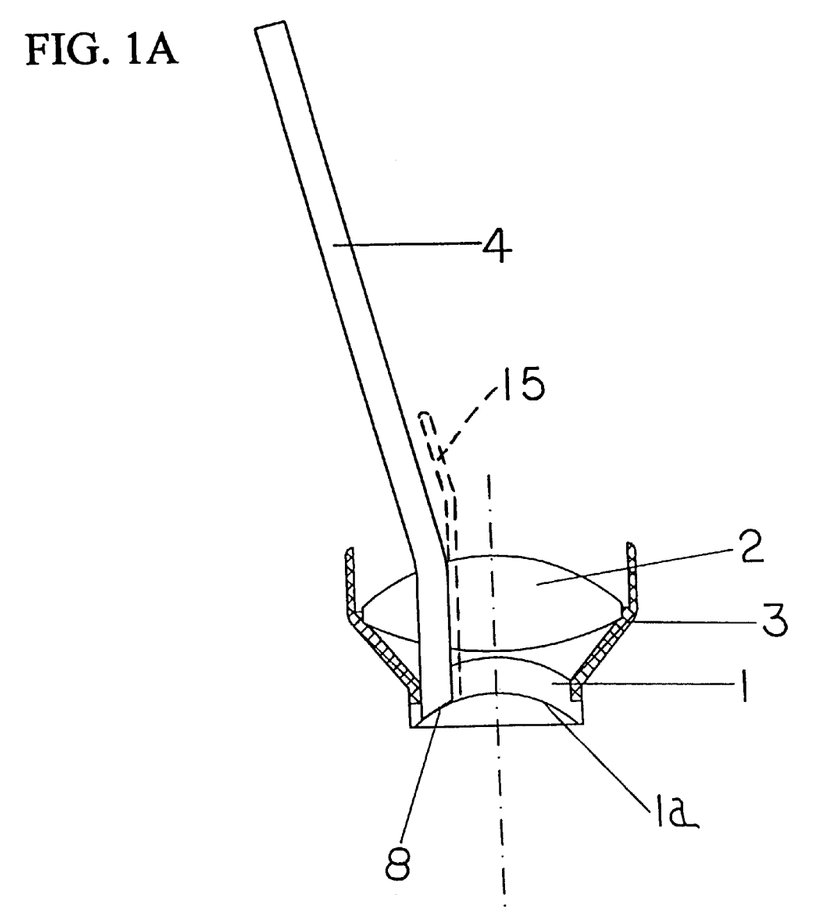
FIGS. 1A and 1B illustrate an exemplary embodiment with a fiber-optic light conductor introduced through a biconcave lens.
Figure 1B:
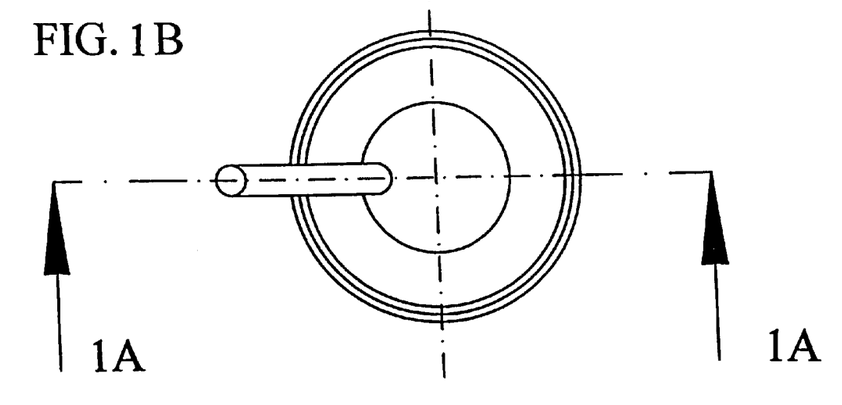
Figure 2A:
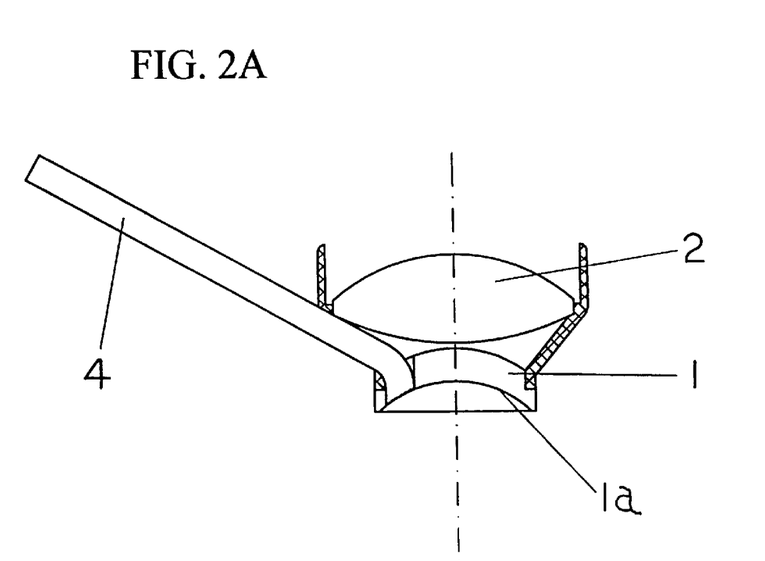
FIGS. 2A and 2B illustrate an exemplary embodiment with a laterally introduced fiber-optic light conductor.
Figure 2B:
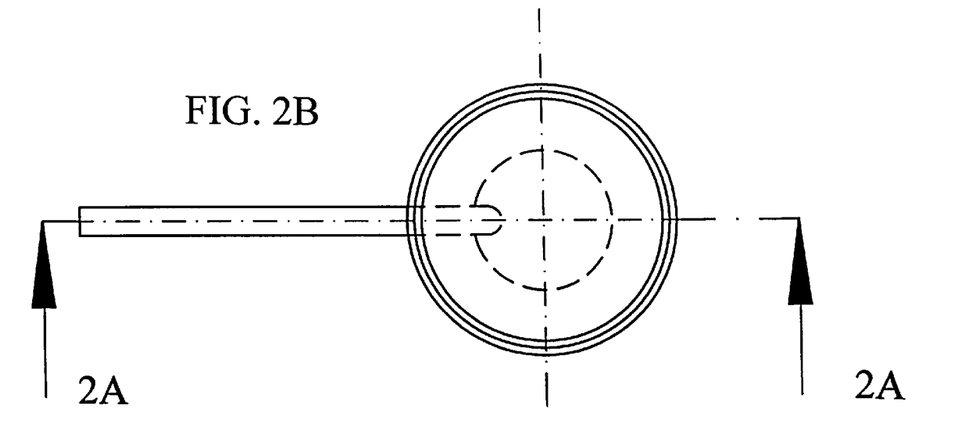

The exemplary embodiment illustrated in FIGS. 2A and 2B differs from the one illustrated in FIGS. 1A and 1B by the fiber-optic light conductor 4 not being guided through the biconcave lens 2 but being introduced laterally through the housing 3 into the optic system.

Figure 3A:
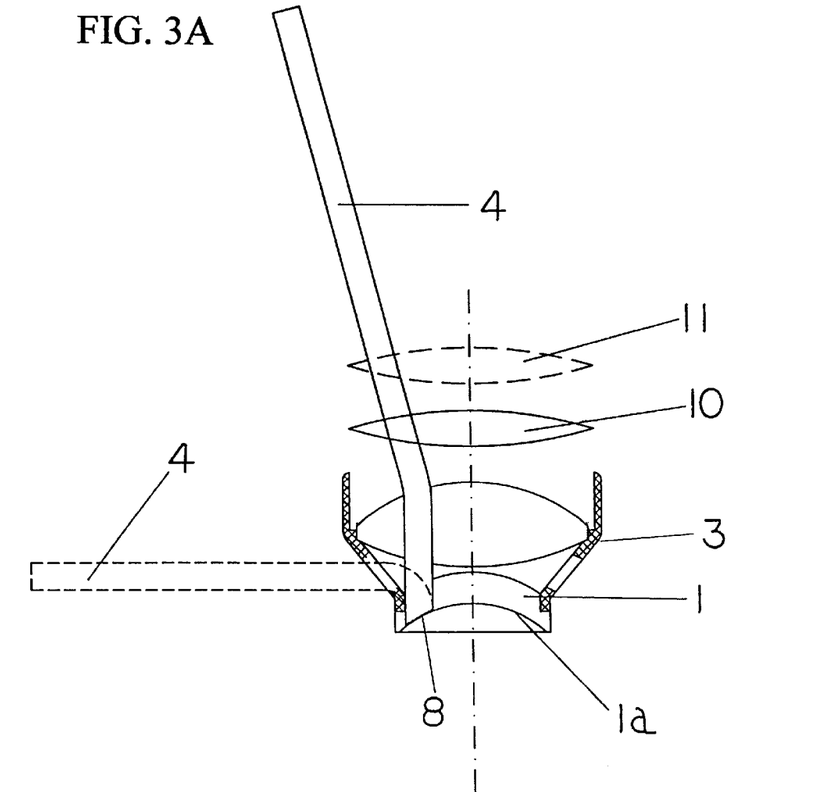
FIGS. 3A and 3B illustrate an exemplary embodiment according to FIGS. 1A and 1B or FIGS. 2A and 2B enlarged with further lenses.
Figure 3B:
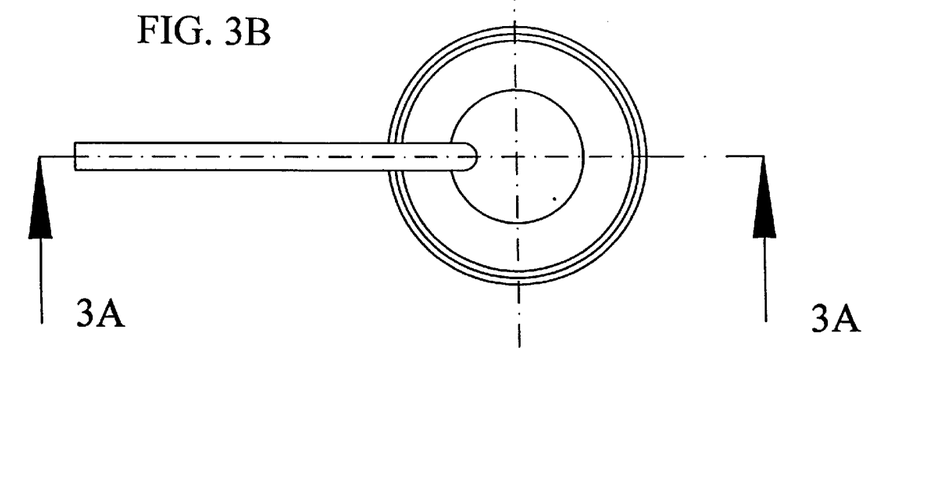

Further lenses 10 and 11 are indicated in FIG. 3A, with which the optic system according to FIGS. 1 and 2 can be enlarged. Not illustrated is the holder into which these lenses 10 and 11 are inserted.

Figure 4A:
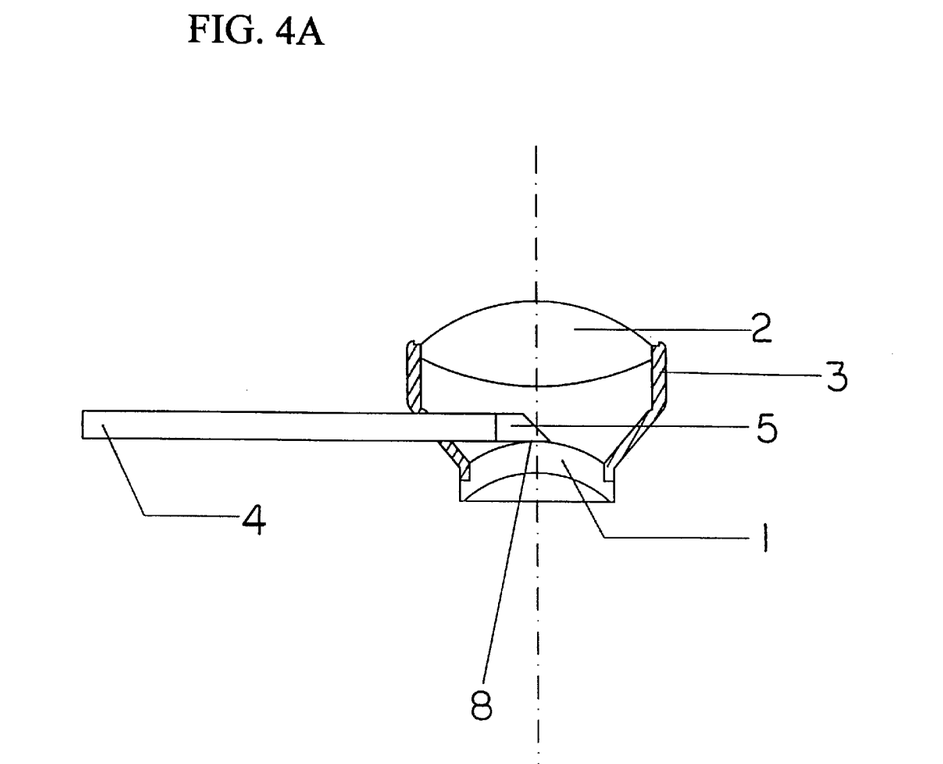
FIGS. 4A and 4B illustrate an exemplary embodiment with a prism mounted on the concave-convex lens.
Figure 4B:
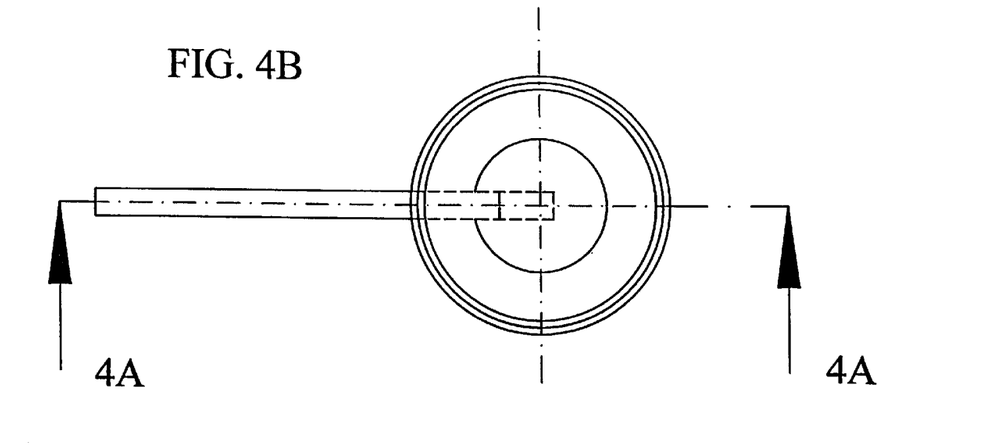

The exemplary embodiment illustrated in FIGS. 4A and 4B has a prism connected, optically guidingly to the concave-convex lens 1 in such a manner that light beams from the fiber-optic light conductor 4, which light beams are guided into the prism 5, are introduced through the light-exiting surface 8 of the prism into the concave-convex lens 1 and from there enter into the eyeball.

Figure 5A:
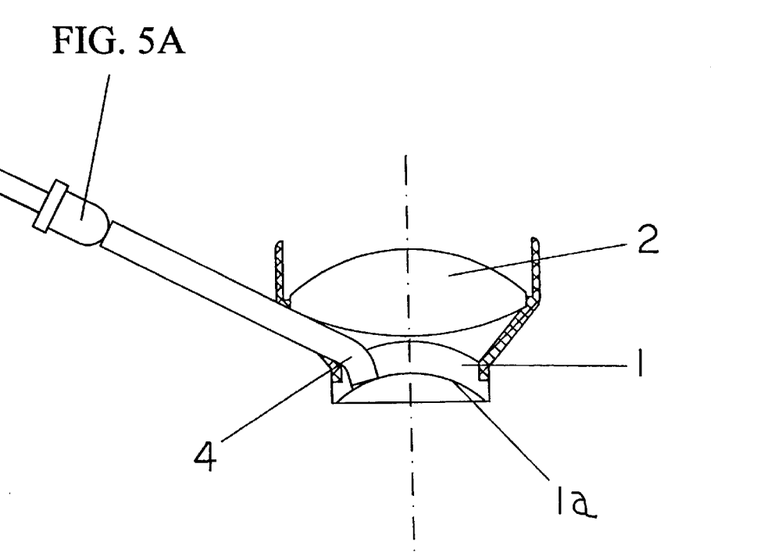
FIGS. 5A and 5B illustrate an exemplary embodiment according to FIG. 2 with a light diode as the light source.
Figure 5B:
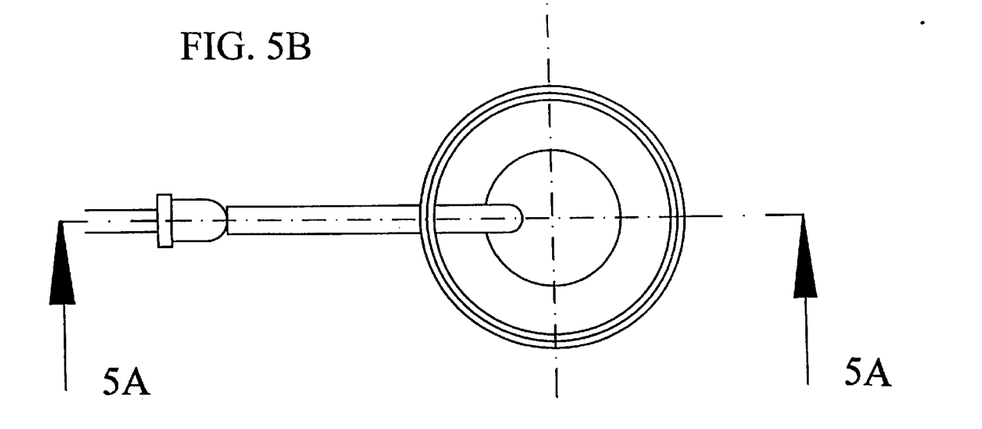

FIGS. 5A and 5B show the exemplary embodiment according to FIG. 2, however, the exemplary embodiment according to FIG. 5 is enlarged by a light source. This light source is a light diode 7.

Figure 6A:
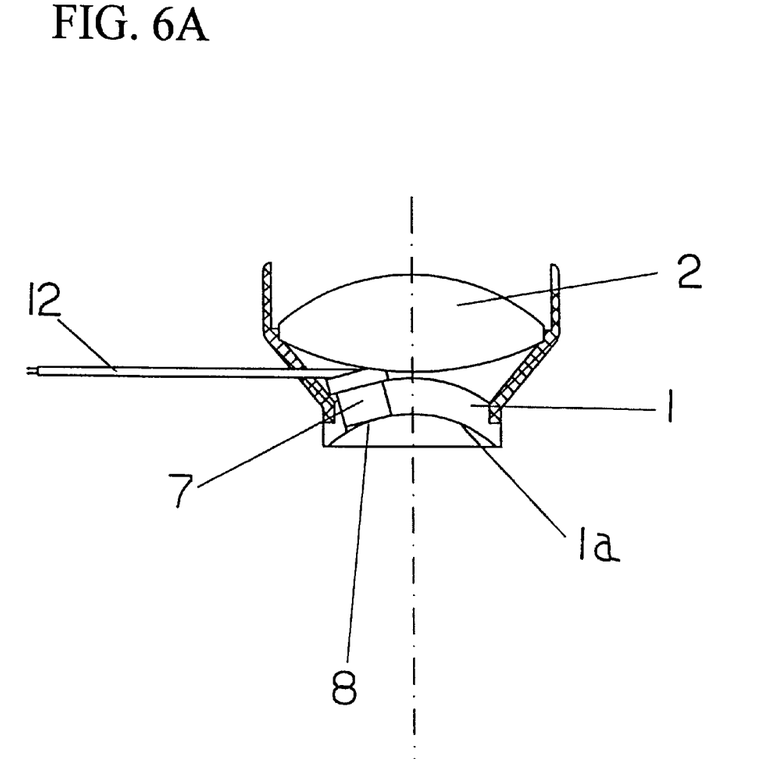
FIGS. 6A and 6B illustrate an exemplary embodiment with a light diode inserted into the concave-convex lens.
Figure 6B:
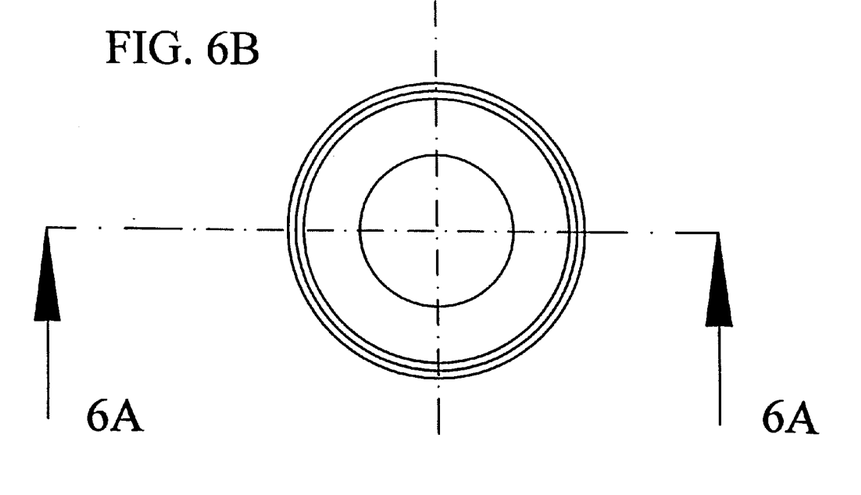

The exemplary embodiment illustrated in FIGS. 6A and 6B has, in contrast to the exemplary embodiments of the preceding figures, a light diode 7 is inserted into the concave-convex lens 1. The light-exiting surface 8 of the light diode terminates flush with the concave lens surface 1a of the concave-convex lens 1. Cables 12 are guided laterally through a wall of the housing 3 in order to supply current to the light diode 7.

Figure 7:
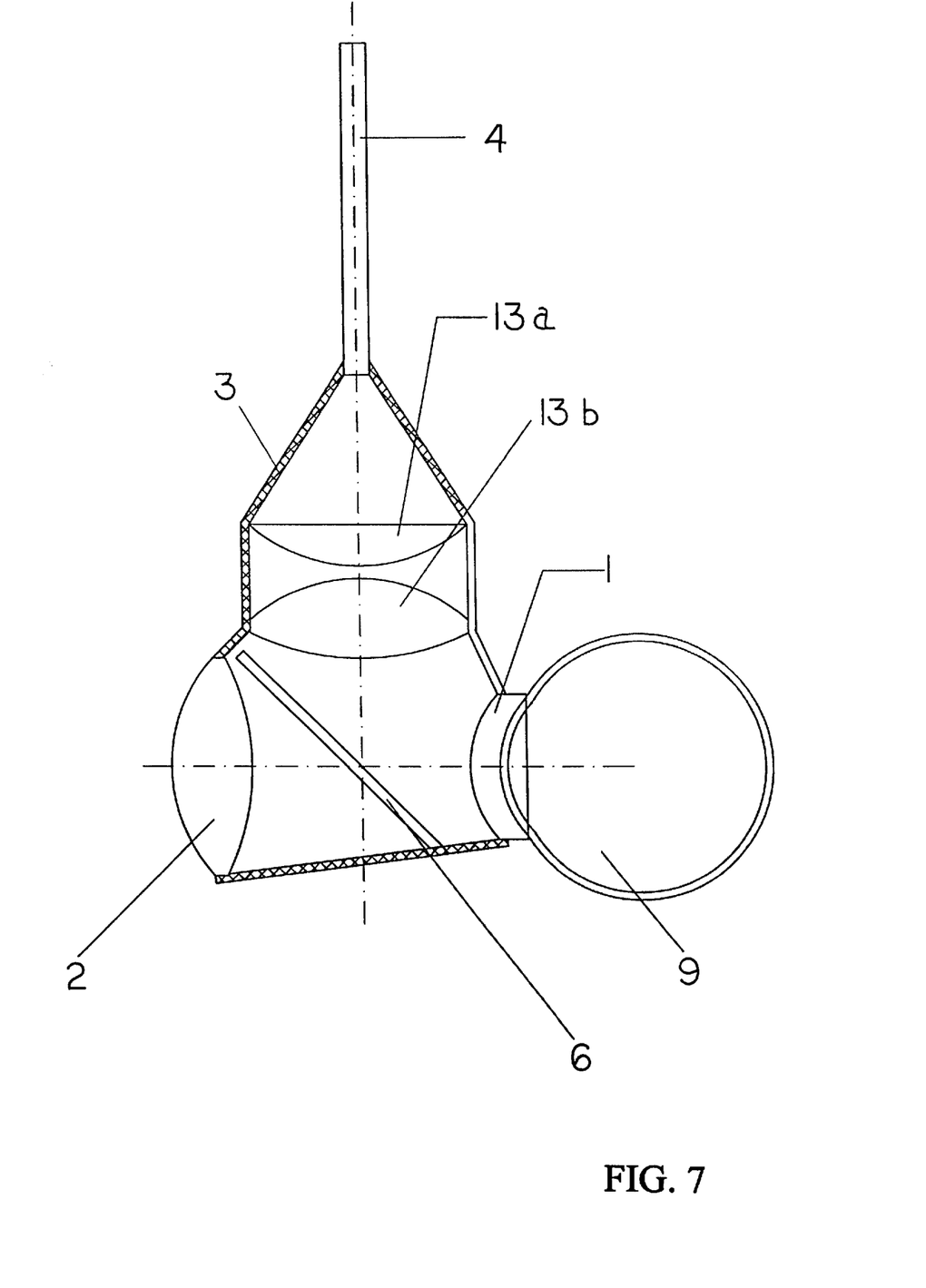
FIG. 7 illustrates an exemplary embodiment with a semi-permeable reflection surface.

The second suggestion for attainment of the purpose of the invention can be realized by an exemplary embodiment according to FIG. 7. The concave-convex lens 1 is placed onto the eyeball 9 again by interjecting an immersion fluid. The light to be reflected, which light exits from the eyeball, enters through the concave-convex lens 1 into the biconcave lens 2. The light passes thereby the semitransparent mirror 6. This semitransparent mirror 6 is used to deflect the light entering laterally through the light inlet into the housing 3. Two collective lenses 13a and 13b are inserted between the mirror 6 and the light inlet. These lenses are used to spread the light exiting from the fiber-optic light conductor 4 so that the light reflected on the semitransparent mirror 6 illuminates an area as wide as possible in the eyeball 9.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. In an optic system for viewing the inside of an eye with a lens system having a first lens with a concave lens surface configured to be placed onto the cornea of an eye, and at least one further lens arranged in viewing direction in front of the first lens, the improvement wherein the optic system has an illuminating device, the light-exiting surface of which lies within the first lens and terminates substantially flush with the concave lens surface of the first lens.

2. The optic system according to claim 1, wherein the light-exiting surface is arched concavely or convexly.

3. The optic system according to claim 1, wherein the light-exiting surface is arched spherically, planely or astigmatically.

4. The optic system according to claim 1, wherein the light-exiting surface of the illuminating device is art of at least one fiber-optic light conductor.

5. The optic system according to claim 4, wherein the fiber-optic light conductor is introduced into the optic system between the first lens and each further lens.

6. The optic system according to claim 4, wherein the fiber-optic light conductor is introduced through the further lens into the optic system.

7. In an optic system for viewing the inside of an eye with a lens system having a first lens with a concave lens surface configured to be placed onto the cornea of an eye, and at least one further lens arranged in viewing direction in front of the first lens, the improvement wherein the optic system has an illuminating device, the light exiting surface of which lies within at least one of the first lens and terminates substantially flush with a lens surface of the first lens, and wherein a hose for an immersion fluid is guided parallel to the fiber-optic light conductor, which hose terminates on the concave side of the first lens.

8. The optic system according to claim 7, wherein the light-exiting surface of the illuminating device is part of at least one fiber-optic light conductor.

9. In an optic system for viewing the inside of the eye with a lens system having a first lens with a concave lens surface configured to be placed onto the cornea of an eye, and at least one further lens arranged in viewing direction in front of the first lens, the improvement wherein a semitransparent reflection surface is inserted between the first lens and the second lens, the main plane of which surface is inclined approximately 45° with respect to the optic axis of the optic system, wherein a lateral light inlet into the optic system is provided in the area of the reflection surface, whereby light beams entering in this manner can be deflected through the semitransparent reflection surface into the viewing direction.

10. The optic system according to claim 9, wherein the reflection surface is a semipermeable mirror.

11. The optic system according to claim 9, wherein the semipermeable reflection surface is formed by at least one prism.

12. The optic system according to claim 9, wherein the semitransparent reflection layer is arched.

13. The optic system according to claim 9, wherein at least a collective lens is inserted between the reflection surface and the light inlet.

14. The optic system according to claim 9, wherein the first lens is a concave-convex lens and the one further lens is a biconvex lens.

15. The optic system according to claim 9, wherein the lenses and the further individual parts of the optic system are releasably assembled in one housing.

16. The optic system according to claim 15, wherein the housing is sealed off and is protected also against stray-light entry.

17. The optic system according to claim 8, wherein the optic system is configured to be sterilized and/or autoclaved.

18. The optic system according to claim 8, wherein the optic system is provided with a holder, into which additional lenses can be inserted.

19. The optic system according to claim 8, wherein the optic system has an image-viewing and/or image-receiving device.

20. In an optic system for viewing the inside of an eye with a lens system having a first lens with a concave lens surface configured to be placed onto the cornea of an eye, and at least one further lens arranged in viewing direction in front of the first lens, the improvement wherein the optic system has an illuminating device, the light-exiting surface of which lies within at least one of the first lens and terminates substantially flush with a lens surface of the first lens and wherein the light-exiting surface of the illuminating devices is a part of a prism connected optically conductingly to at least one fiber-optic light conductor.

21. The optic system according to claim 20, wherein each fiber-optic light conductor is optically connected to a light source.

22. In an optic system for viewing the inside of an eye with a lens system having a first lens with a concave lens surface configured to be placed onto the cornea of an eye, and at least one further lens arranged in viewing direction in front of the first lens, the improvement wherein the optic system has an illuminating device, the light-exiting surface of which lies within at least one of the first lens and terminates substantially flush with a lens surface of the first lens and wherein the light-exiting surface is part of a light source.

23. The optic system according to claim 22, wherein the light source is a light diode.

24. The optic system according to claim 22, wherein the light source is inserted into the first lens.

\* \* \* \* \*

UNITED STATES PATENT AND TRADEMARK OFFICE
CERTIFICATE OF CORRECTION

PATENT NO.    : 6,196,686 B1
DATED         : March 6, 2001
INVENTOR(S)   : Joseph Reiner It is certified that error appears in the above-identified patent and that said Letters Patent is hereby corrected as shown below:

<u>Column 4,</u>
Line 39, change "art" to -- part --.

<u>Column 5,</u>
Lines 25, 27 and 30, change "Claim 8" to -- Claim 9 --.

Signed and Sealed this

Twenty-sixth Day of March, 2002

*Attest:*

*Attesting Officer*

JAMES E. ROGAN
*Director of the United States Patent and Trademark Office*